(12) United States Patent
Klinkenbusch

(10) Patent No.: US 8,954,293 B2
(45) Date of Patent: Feb. 10, 2015

(54) METHOD AND ARRANGEMENT FOR RECONSTRUCTING THE SOURCE OF AN ELECTROMAGNETIC FIELD

(75) Inventor: Ludger Klinkenbusch, Kiel (DE)

(73) Assignee: Christian-Albrechts-Universitat zu Kiel, Kiel (DE)

(*) Notice: Subject to any disclaimer, the term of this patent is extended or adjusted under 35 U.S.C. 154(b) by 524 days.

(21) Appl. No.: 13/383,939

(22) PCT Filed: Jul. 14, 2010

(86) PCT No.: PCT/DE2010/000824
§ 371 (c)(1),
(2), (4) Date: Jan. 13, 2012

(87) PCT Pub. No.: WO2011/006480
PCT Pub. Date: Jan. 20, 2011

(65) Prior Publication Data
US 2012/0116725 A1    May 10, 2012

(30) Foreign Application Priority Data
Jul. 16, 2009 (DE) .......................... 10 2009 033 421

(51) Int. Cl.
*G06F 15/00* (2006.01)
*G01R 29/10* (2006.01)
(Continued)

(52) U.S. Cl.
CPC ............ *G01R 29/10* (2013.01); *A61B 5/04009* (2013.01); *A61B 5/6814* (2013.01); *A61B 5/04004* (2013.01); *A61B 5/0484* (2013.01)
USPC ........... 702/189; 702/179; 343/703; 343/893; 600/409

(58) Field of Classification Search
CPC .. G01R 29/10; A61B 5/04004; A61B 5/6814; A61B 5/0484; A61B 5/04009
USPC ........... 702/189, 179; 343/703, 893; 600/409
See application file for complete search history.

(56) References Cited

U.S. PATENT DOCUMENTS

| 4,201,987 A * | 5/1980 | Tricoles et al. ............... 343/703 |
| 6,377,041 B1 * | 4/2002 | Jones et al. .................... 324/244 |

(Continued)

FOREIGN PATENT DOCUMENTS

| EP | 0710849 A2 | 5/1996 |
| WO | WO00/36428 A1 | 6/2000 |

(Continued)

OTHER PUBLICATIONS

International Preliminary Report on Patentability and the Written Opinion of the International Searching Authority for PCT/DE2010/000824 dated Jan. 17, 2012.
(Continued)

*Primary Examiner* — Carol S Tsai
(74) *Attorney, Agent, or Firm* — Alix, Yale & Ristas, LLP

(57) ABSTRACT

The disclosure relates to a method for reconstructing the source of an electromagnetic field. Firstly, a measurement space separate from the source is selected so that the measurement space is connected to the source via a magnetically homogeneous spatial region. Measured values of the electromagnetic field emitted by the source are recorded on the surface of the measurement space so that the electromagnetic field in the measurement space can be uniquely determined in the context of an error bound determined by the discreteness of the measured values. A mathematical model of the electromagnetic source is developed which has a multiplicity of unknowns, and a system of equations is set up that relates the unknowns of the model to the measured values. The system of equations is solved in order to determine the characteristics of the electromagnetic source. The disclosure also relates to an arrangement for carrying out the method.

13 Claims, 3 Drawing Sheets

(51) Int. Cl.
  *A61B 5/04* (2006.01)
  *A61B 5/00* (2006.01)
  *A61B 5/0484* (2006.01)

(56) References Cited

U.S. PATENT DOCUMENTS

| | | | |
|---|---|---|---|
| 6,762,726 B2* | 7/2004 | Alden et al. | 343/703 |
| 6,768,967 B2* | 7/2004 | Johnson et al. | 702/179 |
| 7,026,997 B2* | 4/2006 | Rahola | 343/700 MS |
| 7,119,739 B1* | 10/2006 | Struckman | 342/174 |
| 7,729,740 B2* | 6/2010 | Kraus et al. | 600/409 |
| 8,471,774 B2* | 6/2013 | Oh et al. | 343/703 |
| 2002/0038196 A1* | 3/2002 | Johnson et al. | 702/179 |
| 2003/0231141 A1* | 12/2003 | Alden et al. | 343/893 |
| 2005/0234329 A1* | 10/2005 | Kraus et al. | 600/409 |

FOREIGN PATENT DOCUMENTS

| | | |
|---|---|---|
| WO | WO03/062840 A1 | 7/2003 |
| WO | WO2009/038388 A1 | 3/2009 |
| WO | WO2009/046516 A1 | 4/2009 |

OTHER PUBLICATIONS

Alvarez, Y. et al., "Reconstruction of Equivalent Currents Distribution Over Arbitrary Three-Dimensional Surfaces Based on Integral Equation Algorithms", IEEE Transactions on Antennas and Propagation, vol. 55, No. 12, Dec. 2007.

Hansen, T. B., "Complex-Point Dipole Formulation of Probe-Corrected Cylindrical and Spherical Near-Field Scanning of Electromagnetic Fields", IEEE Transactions on Antennas and Propagation, vol. 57, No. 3, Mar. 2009.

East, T. W. R., "Spherical Configurations for Near-Field Antenna Measurements", Electrical and Computer Engineering, 1998, IEEE Canadian Conference on Waterloo, Ont., Canada May 24-28, 1998, New York, NY, USA, IEEE, US, vol. 2, May 24, 1998.

Klinkenbusch, L. et al., "Numerical Analysis of Antenna Fields Using Multipole Expansions", Antennas and Propagation, 2006, EUCAP 2006, First European Conference on, IEEE, Piscataway, NJ, USA, Nov. 6, 2006.

Hansen, J. E. (ed.), "Spherical Near-Field Antenna Measurements", IEE Electromagnetic Waves Series; 26; Peter Peregrinus Ltd., 1998.

Hernando, M. M. et al., "EMI Radiated Noise Measurement System Using the Source Reconstruction Technique", IEEE Transactions on Industrial Electronics, vol. 55, No. 9, Sep. 2008.

Balanis, C. A., "Advanced Engineering Electromagnetics", John Wiley & Sons, 1989.

Baillet, S. et al., "Electromagnetic Brain Mapping", IEEE Signal Processing Magazine, Nov. 14-30, 2001.

Klinkenbusch, L., "Brief Review of Spherical-Multipole Analysis in Radio Science", Radio Science Bulletin, 324, Mar. 5-16, 2008.

Jin, J., "The Finite-Element Method in Electromagnetics", John Wiley & Sons, 1993.

* cited by examiner

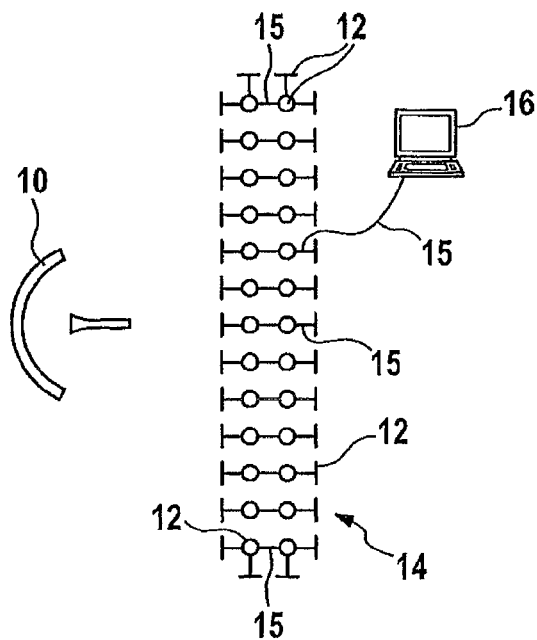
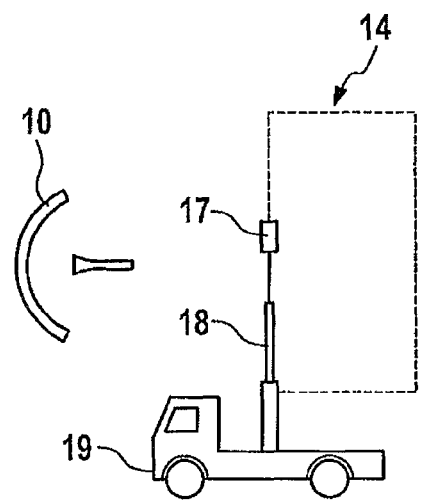
Fig. 1    Fig. 2
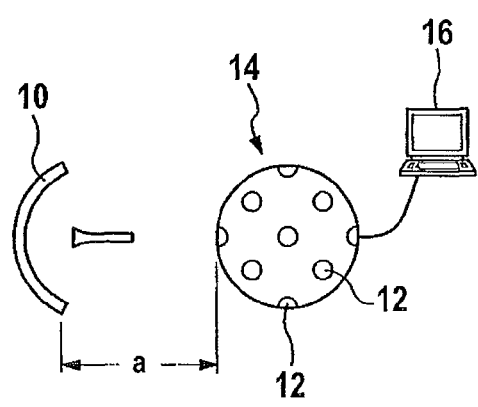
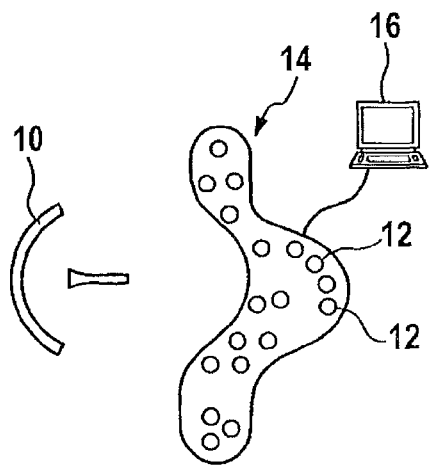
Fig. 3    Fig. 4

METHOD AND ARRANGEMENT FOR RECONSTRUCTING THE SOURCE OF AN ELECTROMAGNETIC FIELD

BACKGROUND

The invention relates to a method for reconstructing the source of an electromagnetic field. The invention also relates to an arrangement for carrying out the method.

According to the laws of electrodynamics, the characteristics of an electromagnetic field inside a closed spatial region can be determined exactly only when specific characteristics of the electromagnetic field are known on a surface completely surrounding the spatial region. Exact determinability is independent of whether or not there is a source of the electromagnetic field in the closed spatial region.

The laws of electrodynamics are based on the supposition of a continuous and gapless knowledge of the characteristics of the electromagnetic field on the surface completely surrounding the spatial region. In technical applications, this assumption is not regularly the case. When the characteristics of an electromagnetic field on a surface are being measured, a multiplicity of measurement sensors are arranged on the surface. The items of information obtained by the measurement sensors and relating to the characteristics of the electromagnetic field on the surface are discrete. Unique determination of the electromagnetic field in the spatial region is also possible on the basis of the discrete measured values but, otherwise than for continuous measured values, no longer in an exact fashion, but only within an error bound. When it is stated in technical applications that an electromagnetic field is being uniquely determined in a closed spatial region by the recording of measured values on the surface thereof, what is always meant is a unique determination in the context of the error bound.

Such measurements are carried out, for example, in order to determine the characteristics of an antenna. To this end, measurement sensors are uniformly distributed on a surface completely surrounding the antenna, for example, a spherical surface, and measured values relating to characteristics of the electromagnetic field emitted by the antenna are recorded. A mathematical model of the antenna is set up, and a field expansion of the electromagnetic field emitted by the antenna is carried out, the coefficients of the field expansion firstly being unknown. With the aid of a system of equations, the unknowns of the field expansion are related to the measured values recorded by the measurement sensors. By solving the system of equations, the characteristics of the antenna can be uniquely calculated within the error bound determined by the discreteness of the measured values (J. E. Hansen (ed.), Spherical Near-Field Antenna Measurements, Peter Peregrinus Ltd., 1988).

It is frequently impossible or attended by an excessive outlay to arrange measurement sensors on a surface completely surrounding the electromagnetic source. This holds, for example, for an antenna near field measurement on a circular cylindrical surface, in the case of which the measurement sensors are arranged for design reasons only on the cylinder envelope, but not on the top and bottom of the cylinder. It is helpful to measure the electromagnetic field as far as possible (for example on the cylinder envelope), and otherwise to proceed on the basis of estimates (for example at the bottom and top). Information relating to the electromagnetic field is then available from the measured values and the estimates, when taken together, for a closed surface surrounding the electromagnetic source. The emission characteristics of the antenna can be uniquely calculated in the context of the error bound caused by the discreteness of the measured values from this information. However, the effect of the estimates is a further inaccuracy, whose extent cannot be exactly determined (C. A. Balanis, Advanced Engineering Electromagnetics, John Wiley & Sons, 1989).

A surface not completely surrounding the sources exists, in particular, for measurements which are undertaken on the human body in the course of magnetoencephalography or magnetocardiography. In magnetoencephalography, the magnetic field around the head is measured, and the brain currents that are the source of the magnetic field are reconstructed. In the case of magnetocardiography, a similar attempt is made to deduce the causative heart currents from magnetic fields around the trunk. In both instances, measurement sensors will need to be arranged inside the human body in order to measure the magnetic field on a surface completely surrounding the source.

Proceeding from the prior art mentioned at the beginning, it is the object of the invention to propose a method and an arrangement for reconstructing the source of an electromagnetic field that are affected by a lesser uncertainty. The object is achieved by the features of the independent claims. Advantageous embodiments are to be found in the subclaims.

SUMMARY

In the case of the inventive method for reconstructing an electromagnetic source, a measurement space separate from the source is selected so that the measurement space is connected to the source via a magnetically homogeneous spatial region. Measured values of the electromagnetic field emitted by the source are recorded on the surface of the measurement space. The measured values are recorded in such a way that the electromagnetic field can be uniquely determined in the context of an error bound determined by the discreteness of the measured values. A mathematical model of the source is developed which has a plurality of unknowns, and a system of equations is set up that relates the unknowns of the model to the measured values. The characteristics of the electromagnetic source can be determined by solving the system of equations.

In the case of the inventive arrangement for reconstructing an electromagnetic source, a plurality of measurement sensors are provided for recording characteristics of the electromagnetic field emitted by the source, said sensors being arranged on the surface of a measurement space separate from the source in such a way that the electromagnetic field in the measurement space can be uniquely determined within an error bound determined by the discreteness of the measured values. The arrangement further comprises a computation module which is designed for solving a system of equations in which a plurality of unknowns of a model of the electromagnetic source are related to the measured values of the measurement sensors in order to determine the characteristics of the electromagnetic source.

A few terms may firstly be explained. A measurement space is separate from the source of an electromagnetic field when the source is not included in the measurement space. A completely closed surface surrounding the measurement space is at a distance from the source. A beam emanating from the midpoint of the electromagnetic source in the direction of the measurement space intersects the surface of the measurement space more than once. A spatial region is denoted as magnetically homogeneous when the magnetic permeability inside the space is substantially constant. This holds, for example, for media such as a vacuum, air and biological tissue. Magnetic homogeneity is sufficient when direct currents are to be reconstructed as sources of a magnetic field. If the source of an electromagnetic field is to be reconstructed, the spatial region must be electromagnetically homogeneous. A spatial region is denoted as electromagnetically homogeneous when the electric permittivity, the electric conductivity and the magnetic permeability inside the space are substantially constant. This holds, for example, for a vacuum and air.

Electrostatic fields and magnetic fields of direct currents (=magnetostatic fields) are understood as limiting cases of the term electromagnetic field. The characteristics of the electromagnetic field that are measured on the surface of the measurement space are those that, according to the laws of electrodynamics, permit a unique reconstruction of a specific source of the electromagnetic field when they are continuously known on a surface completely surrounding the source. Which characteristics of the electromagnetic field these are in the individual case depends on the type of source. If, for example, the electric currents that form the source of a magnetic field are to be reconstructed, it is necessary to know either the tangential component of the magnetic field or the normal component of the magnetic field on the surface. What is required to reconstruct the antenna current as source of an electromagnetic field is to know the tangential component of the electric field, or the tangential component of the magnetic field on a surface completely enclosed in the antenna. If the electromagnetic field is static, it suffices to measure the characteristics at a single instant. If the electromagnetic field varies with time, the measurement must be designed so that it detects the time profile. In the case of a time-discrete recording of measured values, this means, in particular, that the sampling theorem should be satisfied. It is possible to record a multiplicity of measured values or all the measured values at different locations in parallel with one another. The measured values at the various locations can be recorded sequentially in time in the case of static operations or given a periodic time dependence.

Describing the characteristics of an electromagnetic source with a mathematical model is a standard procedure. The precise mathematical model is selected by the expert depending on the circumstances of the individual case. The brain currents as source of a magnetic field can, for example, be modeled as a superposition of N electric dipoles (infinitesimal current filaments) at a known location and with a known polarization, but unknown amplitudes (S. Baillet et al., Electromagnetic Brain Mapping, IEEE Signal Processing Magazine, 14-30, November 2001). The characteristics of the electromagnetic source are explicitly determined with the aid of such a model. If only the electromagnetic field emitted by the source is determined such that the source is uniquely defined by the field, this is likewise denoted as an implicit determination of the source encompassed by the invention. The step of actually calculating the source from the field need not necessarily be carried out in the context of the invention. By way of example, for an antenna as source of an electromagnetic field it is possible as implicit determination to model the emitted electromagnetic field as a superposition of N plane waves of known polarization, but unknown amplitude and phase.

For the actual reconstruction of the electromagnetic source, a mathematical relationship is produced between the unknowns of the model and the measured values recorded on the surface of the measurement space. How the mathematical relationship looks and is represented in detail must be determined as a function of the circumstances of the specific problem. Thus, for example, it can be obvious to develop an electromagnetic field by using spherical surface functions when the surface of the measurement space is spherical, or can be assembled from spherical segments. For otherwise formed measurement spaces, the choice would rather be a plane or cylindrical expansion. Also, the mathematical approach used to produce the relationship between the unknowns of the model and the measured values can differ. Thus, for example, it would be possible firstly to calculate the characteristics of the electromagnetic field at interpolation points lying outside the measurement space so as to provide in the sum of measured values and interpolation points information relating to the electric field on a closed surface around the source. The source can then be reconstructed therefrom in a classical way. In most instances, however, a plurality of equations are set up directly in order to relate the measured values to the unknowns of the model. All these possibilities are covered by the wording "setting up a system of equations". The system of equations is solved using known mathematical methods in order to reconstruct the electromagnetic source.

The invention is based on a fundamental theorem that was developed and published by the inventor a short while ago (L. Klinkenbusch, Brief Review of Spherical-Multipole Analysis in Radio Science, Radio Science Bulletin, 324 (March 2008), 5-16). Accordingly, the electromagnetic field is uniquely determined in an electromagnetically homogeneous domain if the electrical or the magnetic field at an arbitrary point and its infinitesimal surroundings is known in this domain. The theorem can be applied directly to purely magnetic fields as follows: the magnetic field in a magnetically homogeneous domain is uniquely determined if the magnetic field is known at an arbitrary point and its infinitesimal surroundings in this domain. The invention makes use of the theorem for a concrete technical application, specifically the determination of the source of an electromagnetic field from field components obtained by measurement. By contrast with the methods known from the prior art, the advantage consists in that there is no need further to accept in addition to the error caused by the discreteness of the measured values an estimation error resulting from the fact that the necessary measured values are available only in part and, moreover, require to be estimated. The result of the inventive method is affected by a lesser uncertainty. The improved result is achieved with a measurement space that is completely unsuitable according to prior opinion, specifically a measurement space that is arranged near the source to be reconstructed.

The error bound, caused by the discreteness of the measured values, for the determination of the electromagnetic field in the measurement space can, for example, be specified quantitatively in the form of a local square error. The electromagnetic field can then be determined everywhere in the measurement space so accurately that the local square error lies below the error bound. In the case of geometrically simple arrangements, it can be calculated analytically whether an arrangement of measurement sensors on the surface of the measurement space satisfies with reference to a specific error bound the condition that the electromagnetic field in the measurement space can be uniquely determined within the error bound. A geometrically simple arrangement in this sense is, for example, present when the measurement space takes a spherical form (J. E. Hansen (ed.), Spherical Near-Field Antenna Measurements, Peter Peregrinus Ltd., 1988). For the purpose of practical application, it is preferred to proceed such that an error bound is fixed and, starting from the error bound, a distribution of measurement sensors on the surface of the measurement space that satisfies the condition is determined analytically.

For more complex measurement spaces, it is not possible in every case to check whether the condition is satisfied through an analytical calculation with the aid of the mathematical methods currently known. In such instances, the relationship must be determined approximately and by application of suitable numerical methods. For example, to this end high-resolution finite element simulation can firstly be used to calculate in the measurement space a reference field that belongs to an assumed continuous distribution of the measured values. (J. Jin, The Finite-Element Method in Electromagnetics, John Wiley & Sons, 1993). Subsequently, the surface of the measurement space is divided into individual non-overlapping elements so that the sum of these elements covers the entire surface, and that each surface element is assigned a measurement sensor, that is to say a measured value is assigned to the assumed continuous distribution. It can then be calculated with the aid of a further high-resolution finite element simulation whether the electromagnetic field belonging to the discrete measured values deviates in the measurement space from the reference field within the prescribed error bound. If this is not the case, another arrangement of measurement sensors on the surface can be adopted, and it can be determined whether the electromagnetic field is uniquely determined within the error bound by this arrangement of measurement sensors. By carrying out these steps a number of times, it is possible to find an arrangement of measurement sensors that satisfies the desired condition even when it cannot be calculated analytically. By means of a non-sinusoidal time-dependent electromagnetic field, an associated error bound is to be determined for the highest occurring frequency. An error bound is firstly fixed here as well for the practical application, and then the approximation method is used to determine a distribution of measurement sensors on the surface of the measurement space so that the electromagnetic field in the measurement space can be determined uniquely within the error bound. In most instances, the result both for the analytical and for the approximate calculation is an arrangement of measurement sensors which is substantially equally distributed on the surface of the measurement space. However, arrangements of measurement sensors that deviate from the equal distribution are also possible.

Finally, the aim of the inventive method is not to determine the electromagnetic field in the measurement space, but to reconstruct the electromagnetic source. In general, the error bound in the measurement space does not correspond to the error within which the electromagnetic source can be reconstructed. The error bound from the measurement space propagates through the system of equations and has the effect of increasing the error bound for the electromagnetic source. There is probably a weak relationship between the error bound in the measurement space and the error bound of the electromagnetic source which, however, cannot be calculated analytically in all instances. However, it is possible in any case to estimate the way that a predetermined error bound for the electromagnetic sources can be observed when the error bound in the measurement space lies below a specific limit. For practical application, it is preferred to prescribe an error bound for the electromagnetic source, to deduce the associated error bound for the measurement space therefrom and, subsequently, to determine a suitable arrangement of measurement sensors on the surface of the measurement space.

The error propagation from the error bound of the measurement space to the error bound of the electromagnetic source depends substantially on how the measurement space is arranged relative to the electromagnetic source. It may be said in general that the error propagation is reduced when the measurement space is at a relatively small distance from the electromagnetic source. On the other hand, for specific applications in antenna metrology, the distance between the measurement sensors and the electromagnetic source is not allowed to be too small, so as to avoid feedback. A suitable distance between measurement space and electromagnetic source has to be determined individually for each measurement problem. In the case of magnetoencephalography and magnetocardiography, the measurement sensors are outside the body and therefore automatically at a distance from the source. It is expedient in the case of these measurements to arrange the measurement sensors in the immediate surroundings of the body. For measurements on antennas, orientation is obtained from the distance that is selected for classical measurement methods.

Moreover, the error propagation decreases the larger the solid angle in which the measurement space surrounds the electromagnetic source. The solid angle of the closed spherical surface is known to be $4\pi$. Of this, when referred to the midpoint of the electromagnetic source the measurement space preferably covers $\frac{1}{6}$, further preferably $\frac{1}{3}$, further preferably $\frac{1}{2}$, further preferably $\frac{2}{3}$. Inside this solid angle, the condition is to be satisfied that a beam emanating from the midpoint of the electromagnetic source intersects the measurement space at least twice.

The surface of the measurement space can comprise a first area fraction and a second area fraction which are arranged substantially parallel to one another and which together make up more than 50%, preferably more than 70%, furthermore preferably more than 80% of the total surface of the measurement space. The two area fractions can be aligned so that a beam emanating from the electromagnetic source intersects both the first area fraction and the second area fraction. The first area fraction can have a concave form, and the second area fraction a convex form, the concave area fraction being aligned in the direction of the source.

This can be achieved, for example, when the measurement space has the form of a cylindrical shell or of a segment of a spherical shell in the center of which the electromagnetic source is arranged.

Of relevance to the measurement results is, moreover, the thickness of the measurement space, that is to say the distance between the point at which the beam intersects the measurement space for the first time and the point at which the beam intersects the measurement space for the second time. If the thickness is too small, the result is that the measured values are strongly coupled to one another. In order to avoid this, the thickness of the measurement space is preferably at least 0.5 times as large, further preferably at least exactly as large, further preferably at least twice as large as the distance between source and measurement space. Such a large thickness of the measurement space is chosen, in particular, whenever there is also still good signal strength at the remote end of the measurement space. This is regularly the case, for example, for the measurement of antennas. If the electromagnetic source is described by a multipole expansion, a large thickness of the measurement space results in a high sensitivity with reference to the dipole term.

By contrast, if, as in magnetoencephalography and magnetocardiography, the signal strength is small, a small thickness of the measurement space is selected in order to obtain still useful measured values at the remote end of the measurement space as well. The thickness of the measurement space is then preferably smaller than $\frac{1}{2}$, further preferably smaller than $\frac{1}{3}$, further preferably smaller than $\frac{1}{5}$ of the distance between the middle of the source region and the measurement space. If the electromagnetic source is described by a multipole expansion, a small thickness of the measurement space results in a high sensitivity with reference to the higher terms of the expansion.

DESCRIPTION OF THE DRAWINGS

The invention is described by way of example below with the aid of advantageous embodiments and with reference to the attached drawings, in which:

FIG. 1 is a schematic of an antenna and an inventive arrangement;

FIGS. 2 to 4 show the view from FIG. 1 for other embodiments of the invention;

DETAILED DESCRIPTION OF THE PREFERRED EMBODIMENTS

Figure 5:
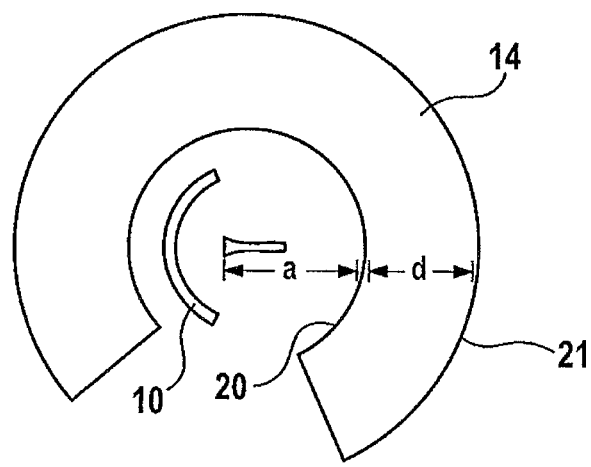
FIG. 5 shows a cross section through an antenna and a measurement space.

In the case of an inventive arrangement in FIG. 1, N measurement sensors 12 are equally distributed on a cuboid surface. The spatial region surrounded by the measurement sensors 12 is denoted as measurement space 14. The electromagnetic field in the measurement space 14 can be determined uniquely with the aid of this arrangement of measurement sensors 12. By applying the described finite element method, it can be calculated within which error bound determination of the electromagnetic field in the measurement space 14 is unique. The N measurement sensors 12 are designed so that they respectively measure amplitude and phase of the electromagnetic field. The measured values are transmitted from the measurement sensors 12 to a computer 16 via signal lines 15.

Arranged at a distance from the measurement space 14 is an antenna 10, which is illustrated schematically in FIG. 1 and in this case is a directional antenna that preferably emits electromagnetic radiation in the direction of the measurement space 14. The spatial region between the measurement space 14 and the antenna 10 is electromagnetically homogeneous. A superposition of N plane electromagnetic waves of known polarization is adopted as mathematical model of the radiation emitted by the antenna 10. The origin of the electromagnetic waves, which corresponds to the location of the antenna 10, is known. Phase and amplitude of the plane waves are unknown.

This mathematical model of the electromagnetic radiation emitted by the antenna 10 is stored in the computer 16. Stored in the computer 16, moreover, is a system of equations which relates the unknowns of the model to the measured values of the measurement sensors 12. Given in each case phase and amplitude of the N plane waves, there are 2*N unknowns in the system of equations. Given the measured values of the N measurement sensors 12, which respectively measure amplitude and phase of the electromagnetic field, the 2*N unknowns are matched by 2*N measured values. It follows from the theorem on which the invention is based that this system of equations has a unique solution. The computer 16 determines this solution using known numerical methods. The result is delivered as unique values for the coefficients of the field expansion. The electromagnetic field emitted by the antenna 10 is thereby uniquely reconstructed in the context of a definable error bound. In particular, it is now possible to calculate the far field of the antenna 10.

Given the unique determination of the emitted electromagnetic field, the characteristics of the antenna 10 itself are also uniquely determined. Where the appropriate calculation actually can be carried out, the characteristics of the antenna 10 would be explicitly determined. If this calculation is given up, the characteristics of the antenna 10 are known only implicitly.

In the embodiment of the invention shown in FIG. 1, all N measurement sensors 12 simultaneously record measured values of the electromagnetic field. If the electromagnetic field has a temporally repeating profile, this is not necessary, but the measured values can also be obtained sequentially. An arrangement that is designed to obtain the measured values sequentially is shown in FIG. 2. A measurement sensor 17 is fastened on a vehicle 19 via a telescopic mechanism 18. The measurement sensor 17 sequentially approaches N specific points on the surface of the measurement space 14, which is indicated by dashes, and respectively records there measured values of phase and amplitude of the electric field emitted by the antenna 10. Considered in sum over all measured values, the information is exactly the same as the measured values recorded in FIG. 1, and so it is possible to carry out an identical calculation.

A superposition of N multipoles is selected in FIG. 3 as mathematical model of the antenna 10. The location of the N multipoles corresponds to the location of the antenna 10, and is therefore known. Unknown, by contrast, are the coefficients of the multipole expansion. In order to be able to determine the coefficients uniquely with a prescribed accuracy, it must be possible for the electromagnetic field to be uniquely determined within an error bound in a measurement space 14 that is at a distance a from the antenna 10. How large the error bound may be in the measurement space 14 can be estimated with known mathematical methods. If a concrete value for the error bound in the measurement space is available in this way, it is firstly possible to select a form of the measurement space suitable for the concrete problem, and subsequently to determine a suitable distribution of measurement sensors on the surface of the measurement space. In the embodiment of FIG. 3, a spherical measurement space proves to be suitable for the problem. The form of the measurement space 14 is indicated in FIG. 3 with a solid line. It is possible to calculate analytically for the spherical form that an arrangement of N measurement sensors 12 equally distributed on the surface of the spherical measurement space 14 suffices for uniquely determining inside the prescribed error bound the electromagnetic field in the measurement space 14. When this information is available, a practical conversion can be approached by firstly distributing the N measurement sensors 12 over the surface of the spherical measurement space 14 in accordance with the calculation. The measurement sensors 12 are designed so that they respectively measure the tangential component of the electric field. This therefore yields N measured values that can be related to the N unknowns in the multipole expansion via a system of equations. In accordance with the theorem on which the invention is based, there is a unique solution for this system of equations. The computer 16 finds this solution and reconstructs thereby the characteristics of the antenna 10 as source of the electromagnetic field.

As in FIG. 3, in FIG. 4 the antenna 10 is modeled as a superposition of N multipoles. Just as in FIG. 3, it is possible to estimate within which error bound the electromagnetic field in the measurement space 14 must be uniquely determinable so that the coefficients of the multipole expansion can be determined with a desired accuracy. In the case of the irregularly formed measurement space 14 of FIG. 4, it is not possible to calculate analytically from the prescribed error bound how the measurement sensors 12 are to be distributed on the surface of the measurement space 14 so that the condition is satisfied. However it is possible to determine the distribution of the measurement sensors 12 by an approximation method such as, for example, the finite element method. To this end, an arbitrary distribution of measurement sensors is assumed and it is checked whether in this distribution the field in the measurement space is uniquely fixed within the error bound. If this is not the case, the same calculation is carried out with another distribution of measurement sensors 12. This step is repeated until a suitable distribution of measurement sensors 12 is found. In the case of the irregularly formed measurement space of FIG. 4, the result is that it is necessary to arrange N measurement sensors 12 on the surface of the measurement space 14 in a specific, but generally not equally distributed, way. The system of equations with which the N measured values are related to the N unknowns of the multipole expansion has a unique solution in accordance with the theorem on which the invention is based.

In order to determine the electromagnetic field, it suffices for the measurement sensors 12 to measure either the tangential component of the electric, or the tangential component of the magnetic field. Both components are measured in FIG. 4. If the determination of the electromagnetic field on the basis of these measured values is carried out twice in a mutually independent fashion, the results can be compared with one another so as to enable an error correction.

In FIG. 5, the antenna 10 emits electromagnetic radiation in an omnidirectional fashion. The form of the measurement space 14 corresponds to a segment of a spherical shell that virtually completely surrounds the antenna 10. The spherical shell has an inner concave area fraction 20 and an outer convex area fraction 21. Together, the concave area fraction 20 and the convex area fraction 21 make up more than 80% of the surface of the measurement space 14. The thickness d of the measurement space 14 corresponds to the distance a between the antenna 10 and the inner concave area fraction 20. The solid angle in which the antenna 10 is surrounded by the measurement space 14 corresponds to more than 90% of the complete sphere. This configuration indicates to carry out a spherical multipole expansion for the antenna 10.

For the purpose of quantification, we may expand the desired electromagnetic field in the case of a time-harmonic procedure for a fixed frequency into a spherical multipole expansion:

$$E(r) = \sum_{n=1}^{L} \sum_{m=-n}^{n} \left[ a_{n,m} N_{n,m}(r) + \frac{Z}{j} b_{n,m} M_{n,m}(r) \right] \quad (1)$$

$$H(r) = \sum_{n=1}^{L} \sum_{m=-n}^{n} \left[ \frac{j}{Z} a_{n,m} M_{n,m}(r) + b_{n,m} N_{n,m}(r) \right]$$

wherein:
E(r), H(r) phasers of the electric and magnetic field strengths (in volt/meter or ampere/meter) at location r (described by the spherical coordinates (r, θ, φ) with reference to a selected coordinate origin,
n, m order n or degree m of the multipole expansion,
$a_{n,m}$, $b_{n,m}$ multipole amplitudes (expansion coefficients),
j imaginary unit,
Z field impedance of free space, in air approximately 377 ohms,
$M_{n,m}$, $N_{n,m}$ expansion functions for the radial (r) and the transverse (θ, φ) components.

The higher the upper bound of the order in (1) is selected, the more accurately is the field resolved. An antenna with a complex directional characteristic is characterized by a relatively large L. For a given L, it is necessary to determine a total of $$2(3+5+\ldots+2L+1)=2L(L+2) \quad (2)$$

unknown multipole amplitudes. The unique determination requires at least just as many independent measurement points on the surface. These are distributed on the entire measurement surface such that a uniform distribution is carried out on a spherical surface around the selected coordinate origin. If, as indicated in FIG. 5, two spherical shells with radii $r_1$ and $r_2$ are involved on the entire scan surface, the total number of the scanning points is distributed uniformly over both shells. In the case of two spherical shells on the surface $r_1$ or $r_2$, it therefore holds for the density of the scanning points p (number of scanning points per unit surface) that:

$$\rho_{1,2} = \frac{L(L+2)}{4\pi r_{1,2}^2} \quad (3)$$

so that the following estimate holds for the mean distance between two neighboring scanning points on a spherical shell:

$$a \approx r. \quad (4)$$

For other scan surfaces, (3) and (4) are to be considered correspondingly; for example, the results on the two radial segments in FIG. 3 are an also decreasing density of the measurement points in accordance with (3) and an increasing distance in accordance with (4).

Particularly in the case of small useful amplitudes of the measured field strength, it is important to eliminate systematic disturbances (for example the Earth's magnetic field). This can be achieved by suitable filtering (in the time domain) as preparation of the actual solution of the problem. In the case of systematic errors that can be assigned a specific spatial source (for example, door slits in a shielded room), the associated spatial frequency spectrum (that is to say, the multipole amplitudes of the associated interference field) is determined in accordance with eq. (1) and subtracted from the multipole amplitudes calculated overall on the basis of the linearity of the medium. Correspondingly, it is possible to calibrate the measurement arrangement by firstly measuring without the useful sources (for example, without patients in the case of magnetoencephalography), and subtracting the multipole amplitudes thus determined from those measured overall.

Figure 6:
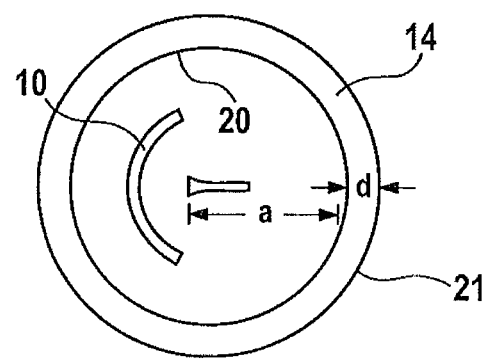
FIG. 6 shows the view from FIG. 5 for another embodiment of the invention.

In the embodiment of FIG. 6, the antenna 10 is an omnidirectional antenna. The measurement space 14 has the form of a cylindrical shell at the center of which the antenna 10 is arranged. Bottom and top of the cylindrical shape are not a constituent of the measurement space 14. Here, as well, the measurement space 14 comprises a concave inner surface 20 and a convex outer surface 21. The thickness d of the measurement space 14 is small by comparison with the distance a between the antenna 10 and the concave inner surface 20. In the case of this problem, the model of the antenna 10 will be expanded using cylindrical wave functions.

Figure 7:
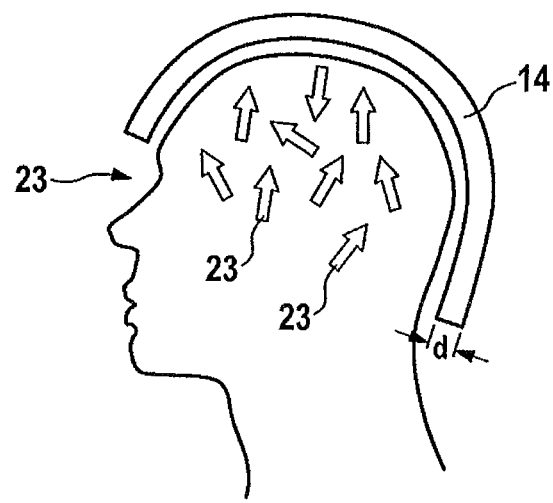
FIG. 7 shows an inventive arrangement being applied in magnetoencephalography.

An application of the invention in magnetoencephalography is shown in FIG. 7. In magnetoencephalography, the aim is to determine the electrical brain currents 23 in the head 22 of a patient that are the source of a magnetic field measured in the surroundings of the head 22. The brain currents 23 are indicated in FIG. 7 by arrows. A measurement space 14 that has the shape of a segment of a spherical shell is arranged so that it surrounds the head 22 of the patient as closely as possible. The space between the measurement space 14 and the brain currents 23 includes different media, specifically air and biological tissue. The media have a substantially identical magnetic permeability, and so for the purpose of the invention the measurement space 14 is connected to the brain currents 23 via a magnetically homogeneous spatial region. The fact that the signal strength is low with this type of measurement means that the measurement space 14 has a small thickness d.

The brain currents that form the source of the magnetic field are modeled by N electrical dipoles $c_i = c_i \hat{e}_i$ with known polarizations $\hat{e}_i$ and with unknown amplitudes (those to be sought) $c_i$ (i=1, 2, 3, . . . , N) at known locations $s_i$. Each of these dipoles produces a magnetic flux density B that can be specified using the Biot-Savart law at the location $r_k$ in accordance with $$B_i(r_k) = \frac{\mu_0}{4\pi} \frac{c_i \times (r_k - s_i)}{|r_k - s_i|^3} = \overline{M}_{ki}(c_i) \qquad (1)$$

$\mu_0 = 4\pi 10^{-7}$ Vs/Am denotes the magnetic permeability of the vacuum. Because of the magnetic linearity of the media considered here (air or biological tissue behaves magnetically like a vacuum) the magnetic fields of all N dipoles at the location $r_k$ are superimposed on one another to form the total field $$B(r_k) = \sum_{i=1}^{N} B_i(r_k).$$

According to the laws of algebra, there is a need for exactly N linearly independent measured values of the magnetic field in order to uniquely determine N dipole amplitudes, that is to say measured values at locations $r_k$ where k=1, 2, 3, . . . , N. These measurement locations are now laid suitably on the surface of the measurement space 14 in FIG. 7 (for example distributed equidistantly). According to the laws of electrodynamics, it suffices respectively to have knowledge of the total magnetic field B($r_k$) only of the field components that are tangentially or normally directed with reference to the measurement surface. Assuming that only the normal field components $B_n(r_k)$ are present, we obtain the system of linear equations $$\begin{pmatrix} B_n(r_1) \\ B_n(r_2) \\ B_n(r_3) \\ \vdots \\ B_n(r_N) \end{pmatrix} = \begin{pmatrix} \overline{M}^n_{11} & \overline{M}^n_{12} & \tilde{M}^n_{13} & \cdots & \overline{M}^n_{1N} \\ \tilde{M}^n_{21} & \tilde{M}^n_{22} & \tilde{M}^n_{23} & \cdots & \tilde{M}^n_{2N} \\ \overline{M}^n_{31} & \overline{M}^n_{32} & \tilde{M}^n_{33} & \cdots & \tilde{M}^n_{3N} \\ \vdots & \vdots & \vdots & \ddots & \vdots \\ \overline{M}^n_{N1} & \overline{M}^n_{N2} & \tilde{M}^n_{N3} & \cdots & \tilde{M}^n_{NN} \end{pmatrix} \cdot \begin{pmatrix} c(s_1) \\ c(s_2) \\ c(s_3) \\ \vdots \\ c(s_N) \end{pmatrix} \qquad (2)$$

In the matrix elements, the upper index n is intended to symbolize the sole consideration of the normal components. The amplitudes being sought for the dipoles are now determined by suitable methods from linear algebra by solving the system of linear equations.

If, in addition, the locations $r_k$ of the N dipoles are unknown, it is possible to use various assumed locations $r_k$ to attempt to solve the system of equations. A unique solution of the system of equations is obtained in accordance with the theorem, on which the invention is based, precisely when the locations $r_k$ are correctly assumed. This renders it possible to determine the correct locations $r_k$ by iteration.

Figure 8:
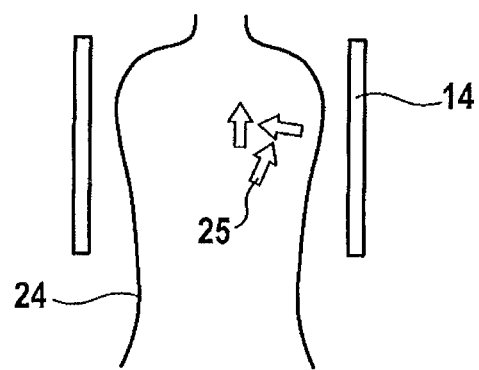
FIG. 8 shows an inventive arrangement being applied in magnetocardiography.

The invention is applied in the field of magnetocardiography in FIG. 8. The aim of this application is to identify the heart currents as source of a magnetic field. A trunk 24 of a patient with heart currents 25 indicated is shown schematically. A measurement space 14 that has the shape of a cylindrical shell surrounds the trunk 24 of the patient. Just as in the case of the magnetoencephalography that has just been described in detail, the heart currents, which are modeled as superposition of N dipoles, can be inferred from measured values of the normal or tangential component of the magnetic field on the surface of the measurement space 14.

The invention claimed is:

1. A method for reconstructing the source of an electromagnetic field, having the following steps:
    a. selecting a measurement space separate from the source so that the measurement space is connected to the source via a magnetically homogeneous spatial region;
    b. recording measured values of the electromagnetic field emitted by the source on the surface of the measurement space in such a way that the electromagnetic field in the measurement space can be uniquely determined in the context of an error bound determined by the discreteness of the measured values;
    c. determining a mathematical model of the electromagnetic source which has a multiplicity of unknowns;
    d. setting up a system of equations that relates the unknowns of the model to the measured values; and
    e. solving the system of equations in order to determine the characteristics of the electromagnetic source.

2. The method of claim 1, wherein before step b. an error bound is fixed and a distribution of measurement sensors on the surface of the measurement space is determined analytically, so that the electromagnetic field in the measurement space can be uniquely determined within the error bound.

3. The method of claim 1, wherein before step b. an error bound is fixed and a distribution of measurement sensors on the surface of the measurement space is determined by means of an approximation method so that the electromagnetic field in the measurement space can be uniquely determined within the error bound.

4. The method of claim 1, wherein a multiplicity of measured values are recorded in parallel at different locations in step b.

5. The method of claim 1, wherein in step b. a multiplicity of measured values are recorded at different locations sequentially in time.

6. An arrangement for reconstructing the source of an electromagnetic field having a multiplicity of measurement sensors for recording characteristics of the electromagnetic field emitted by the source, the measurement sensors being arranged on the surface of a measurement space separate from the source in such a way that the electromagnetic field in the measurement space can be uniquely determined within an error bound determined by the discreteness of the measured values, and having a computation module which is designed for solving a system of equations in which a multiplicity of unknowns of a model of the electromagnetic source are related to the measured values of the measurement sensors in order to determine the characteristics of the electromagnetic source.

7. The arrangement of claim 6, wherein the surface of the measurement space comprises a first area fraction and a second area fraction which are arranged substantially parallel to one another and which together make up more than 50%, preferably more than 70%, furthermore preferably more than 80% of the total surface of the measurement space.

8. The arrangement of claim 6, wherein the first area fraction is concave, and the second area fraction is convex.

9. The arrangement of claim 8, wherein the first area fraction is aligned in the direction of the electromagnetic source.

10. The arrangement of claim 6, wherein starting from the midpoint of the electromagnetic source the measurement space covers a solid angle that in relation to the complete sphere is at least ⅓, preferably at least ½, further preferably at least ⅔.

11. The arrangement of claim 6, wherein the measurement space has the form of a segment of a spherical shell.

12. The arrangement of claim 6, wherein the measurement space has the form of a cylindrical shell.

13. The arrangement of claim 6, wherein the sensors are substantially equally distributed on the surface of the measurement space.

* * * * *